United States Patent [19]

Gaffney

[11] Patent Number: 5,093,542
[45] Date of Patent: Mar. 3, 1992

[54] METHANE CONVERSION PROCESS

[75] Inventor: Anne M. Gaffney, West Chester, Pa.

[73] Assignee: Atlantic Richfield Company, Los Angeles, Calif.

[21] Appl. No.: 603,099

[22] Filed: Oct. 25, 1990

Related U.S. Application Data

[62] Division of Ser. No. 738,114, May 24, 1985.

[51] Int. Cl.$^5$ ................................................ C07C 2/00
[52] U.S. Cl. .................................... 585/500; 585/943; 585/654; 585/656; 585/658; 585/661; 585/415; 585/417; 585/418; 585/700
[58] Field of Search ............... 585/500, 943, 654, 656, 585/658, 661, 415, 417, 418, 700

[56] References Cited

U.S. PATENT DOCUMENTS

| | | | |
|---|---|---|---|
| 4,199,533 | 4/1980 | Bensen | 585/500 |
| 4,450,310 | 5/1984 | Fox et al. | 585/943 |
| 4,467,130 | 8/1984 | Olah | 585/943 |
| 4,523,049 | 6/1985 | Liner et al. | 585/500 |

OTHER PUBLICATIONS

Keller and Bhasin, Synthesis of Ethylene via Oxidative Coupling of Methane, J. of Catalysis 73, 9-19 (1982).

*Primary Examiner*—Patrick P. Garvin
*Assistant Examiner*—E. D. Irzinski
*Attorney, Agent, or Firm*—Craig E. Larson

[57] ABSTRACT

A method for converting methane to higher hydrocarbon products and coproduct water wherein a gas comprising methane and a gaseous oxidant are contacted with a nonacidic catalyst at temperatures within the range of about 700° to 1200° C. in the presence of a halogen promoter, the contacting being conducted in the substantial absence of alkali metals or compounds thereof.

13 Claims, No Drawings

METHANE CONVERSION PROCESS

This is a division of application Ser. No. 06/738,114, filed May 24, 1985.

BACKGROUND OF THE INVENTION

This invention relates to the synthesis of hydrocarbons from a methane source. A particular application of this invention is a method for converting natural gas to more readily transportable material.

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example, the methane content of natural gas may vary within the range from about 40 to about 95 volume percent. Other constituents of natural gas include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large scale use of natural gas often requires a sophisticated and extensive pipeline system. Liquefaction has also been employed as a transportation means, but processes for liquefying, transporting, and revaporizing natural gas are complex, energy-intensive and require extensive safety precautions. Transport of natural gas has been a continuing problem in the exploitation of natural gas resources. It would be extremely valuable to be able to convert methane (e.g., natural gas) to more readily handleable or transportable products. Moreover, direct conversion to olefins such as ethylene or propylene would be extremely valuable to the chemical industry.

U.S. Pat. No. 4,199,533 discloses a process for converting methane to higher molecular weight hydrocarbons by using chlorine gas as a recyclable catalyst. The process produces ethylene as a major product along with hydrogen chloride, which is converted to chlorine for recycle in the system. Major drawbacks of the '533 process are the large amount of chlorine required, the necessity of regenerating chlorine from hydrogen chloride to maintain an economically viable system, and the need to use operating temperatures in excess of 1000° C. to produce ethylene.

Recently, it has been discovered that methane may be converted to higher hydrocarbons (e.g., ethane, ethylene and higher homologs) with minimal formation of carbon oxides by contacting methane with a reducible metal oxide as a selective oxygen source. As the methane is converted to hydrocarbon products and coproduct water, the active oxygen of the metal oxide is depleted, resulting in a reduced metal oxide. The reduced metal oxide is relatively inactive for the oxidative conversion of methane but active oxygen may be replaced by regeneration of a reducible metal oxide. Such regeneration is accomplished by reoxidation of the reduced metal oxide.

Reducible oxides of several metals have been identified which are capable of converting methane to higher hydrocarbons. Oxides of manganese, tin, indium, germanium, lead, antimony and bismuth are particularly useful. See U.S. Pat. Nos. 4,443,649; 4,444,984; 4,443,648; 4,443,645; 4,443,647; 4,443,644; and 4,443,646. Also see U.S. Pat. Nos. 4,499,323 and 4,499,324.

U.S. Pat. No. 4,499,322 discloses and claims a process for the conversion of methane to higher hydrocarbon which comprises contacting methane oxidative synthesizing agent containing a promoting amount of alkali metal and/or compounds thereof.

U.S. Pat. No. 4,495,374 discloses and claims a process for the conversion of methane to higher hydrocarbons which comprises contacting methane with an oxidative synthesizing agent containing a promoting amount of alkaline earth metal and/or compounds thereof.

Hinsen and Baerns report studies of a continuous mode for the oxidative coupling of methane wherein regenerating air is cofed with the methane feed. Hinsen, W. and Baerns, M. "Oxidative Koppling von Methan zu $C_2$-Kohlenwasserstoffen in Gegenwart unterschiedlicher Katalysatoren", Chemiker-Zeitung, Vol. 107, No. 718, pp. 223–226 (1983). Using a catalyst based on lead oxide and gamma-alumina in a fixed bed reactor operated at 1 atmosphere total pressure and 600°–750° C., they report results of approximately 53% selectively to ethane and ethylene at 8% methane conversion for a feed consisting of about 50% methane, 25% air and 25% nitrogen. Other metal oxides studies by Hinsen and Baerns included oxides of Bi, Sb, Sn and Mn.

Commonly-assigned U.S. patent application Ser. No. 600,656, filed Apr. 16, 1984, discloses and claims a process for converting methane to higher hydrocarbons which comprises contacting methane and an oxygen-containing gas with a solid comprising a reducible metal oxide and an alkali/alkaline earth metal promoter.

Commonly-assigned U.S. patent application Ser. No. 600,670, filed Apr. 16, 1984, discloses and claims a process for converting methane to higher hydrocarbons which comprises contacting methane and an oxygen-containing gas with a manganese silicate.

Concurrently-filed, commonly-assigned U.S. patent application Ser. No. discloses and claims a method for converting methane to higher hydrocarbons wherein methane and a gaseous oxidant are contacted with a nonacidic solid. In a preferred embodiment, the solid comprises an alkali metal component associated with a support material. The application also teaches conducting the contacting in the presence of halogen promoters when employing alkali-promoted solids.

Oxidative condensation of methane in the presence of solids superacid catalysts is disclosed in U.S. Pat. Nos. 4,433,192; 4,465,893; and 4,467,130. European Published Patent Application 93,543 discloses a process for aromatizing methane wherein a methane feedstock and an oxidizing agent other than molecular oxygen are contacted at temperatures of about 10° to 600° C. with a solid acidic catalyst having Bronsted acid sites.

The reaction products of such processes are hydrocarbons, carbon oxides, coke and water. It would be beneficial in these processes to reduce selectivities to carbon oxides and coke and to increase methane conversions to the desired hydrocarbon products. Accordingly, an object of this invention is to provide an improved process for converting methane to higher hydrocarbons. More particular aspects, objects and the several advantages of this invention will become apparent to those skilled in the art upon reading this disclosure and the appended claims.

SUMMARY OF THE INVENTION

It has now been found that methane may be converted to higher hydrocarbons by contacting a gas comprising methane and a gaseous oxidant with a nonacidic solid at a temperature within the range of about 700° to 1200° C. in the presence of a promoter selected from the group consisting of halogens and compounds thereof, said contacting being conducted in the substantial absence of alkali metals or compounds thereof. The promoter may be incorporated into the catalyst prior to conducting the contacting, but preferably the promoter is introduced with methane and gaseous oxidant while conducting the contacting. Halogens are selected from the group consisting of F, Cl, Br and I. Presently preferred promoters are chlorine, bromine and compounds thereof. Chlorine and compounds of chlorine are particularly preferred.

A desired characteristic of the solid catalyst is that it be substantially nonreducible under process conditions. While a characteristic of the present process is coproduction of water, the present process does not require the presence of reducible metal oxides.

The catalytic process of this invention offers the advantage of employing simpler, less complex solid systems than those processes, described above, which employ solids comprising reducible metal oxides. Moreover, use of nonacidic catalysts minimizes the coking and product decomposition problems encountered with acidic systems. Furthermore, conducting the contacting in the substantial absence of alkali metal promoters has been found to enhance the formation of unsaturated products: the ratio of ethylene-to-ethane in the effluent produced by the present process is higher, thus producing an effluent more amenable to further conversion to normally liquid hydrocarbons.

DETAILED DESCRIPTION OF THE INVENTION

In addition to methane the hydrocarbon feedstock employed in the method of this invention may contain other hydrocarbon or non-hydrocarbon components. The methane content of the feedstock, however, will typically be within the range of about 40 to 100 vol. %, preferably within the range of about 80 to 100 vol. %, more preferably within the range of about 90 to 100 vol. %.

The gaseous oxidant is selected from the group consisting of molecular oxygen, oxides of nitrogen, and mixtures thereof. Preferably, the gaseous oxidant is an oxygen-containing gas. A preferred oxygen-containing gas is air. Suitable oxides of nitrogen include $N_2O$, NO, $N_2O_3$, $N_2O_5$ and $NO_2$. Nitrous oxide ($N_2O$) is a presently preferred oxide of nitrogen.

The ratio of hydrocarbon feedstock to gaseous oxidant gas is not narrowly critical to the present invention. However, the ratio will desirably be controlled to avoid the formation of gaseous mixtures within the flammable region. The volume ratio of hydrocarbon/gaseous oxidant is preferably within the range of about 0.1–100:1, more preferably within the range of about 1–50:1. Methane/gaseous oxidant feed mixtures containing about 50 to 90 volume % methane have been found to comprise a desirable feedstream.

The solid employed in this invention is generally characterized as "nonacidic". This desciptor is meant to refer to the main, predominant surface properties of the solids. For example some solid bases are known to have acidic properties to some extent. See Tanabe, K., "Solid Acid and Base Catalysts." In: Catalysis Science & Technology, vol. 2 (New York, Springer - Verlag Berlin Heidelberg, 1981). Currently preferred solids used in the present process are characterized by negligible acidity (less than about 0.01 meq/gm) in the $H_o$ range less than about 3.3, preferably less than about 6.8. $H_o$ is the Hammett acidity parameter described on pp. 234–241 of Tanabe.

A further characteristic of preferred solids for the present process is a relatively low surface area. Solids having surface areas less than about 50 $cm^2$/gm are suitable, but the surface areas of preferred solids are within the range of about 0.1–10 $m^2$/gm.

A still further characteristic of preferred solids for the present process is that they be stable and substantially nonreducible under process conditions. Examples of suitable solids include those solid bases described in Table 2 on p. 233 of Tanabe, supra. However, presently preferred solids are metal oxides and mixed oxides. Alkaline earth oxides are particularly preferred, especially MgO and CaO. Other suitable metal oxides are $SiO_2$, alpha-$Al_2O_3$, $La_2O_3$, $ThO_2$, $TiO_2$, and $ZrO_2$. Such materials are relatively stable under the conditions of the present process.

Halogen promoters are preferably introduced into the process with gaseous feedstreams flowing to the process. Any suitable concentration of promoter can be used. The promoter can be introduced continuously or periodically, although continuous introduction is preferred. Suitable sources of halogen include free halogen gas, hydrogen halides, ammonium halides, aliphatic halides (e.g., methyl halide, methylene halide, ethyl halide, amyl halide, allyl halide), cycloaliphatic halides (e.g., cyclohexyl halide), halogen substituted aliphatic acids such as methyl amine hydrochloride, and the like. Mixtures of various halogen sources may be used. Presently preferred are free halogen gas, aliphatic halides and hydrogen halides. Methane/gaseous oxidant feed mixtures containing about 0.01 to 10 vol. % halogen promoter, preferably 0.1 to 5 vol. %, are desirable feedstreams.

Preferably, methane and oxygen are contacted with the agent in the substantial absence of catalytically effective nickel, noble metals and compounds thereof. (i.e., nickel, rhodium, palladium, silver, osmium, iridium, platinum and gold) to minimize the deleterious catalytic effects thereof. These metals, when contacted with methane at the temperatures employed in the first step of the present invention, tend to promote coke formation, and the metal oxides tend to promote the formation of combustion products rather than the desired hydrocarbons. The term "catalytically effective" is used herein to identify that quantity of one or more of nickel and of the noble metals and compounds thereof which substantially changes the distribution of products obtained in the method of this invention relative to such contacting in the absence of such metals and compounds thereof.

Operating temperatures for the method of this invention are generally within the range of about 700° to 1200° C., more preferably within the range of about 800° to 1000° C.

Operating pressures are not critical to the presently claimed invention. However, both general system pressure and partial pressures of methane and oxygen have been found to effect overall results. Preferred operating pressures are within the range of about 0.1 to 30 atmospheres.

The space velocity of the gaseous reaction streams are similarly not critical to the presently claimed invention, but have been found to effect overall results. Preferred total gas hourly space velocities are within the range of about 10 to 100,000 hr.$^{-1}$, more preferably within the range of about 600 to 40,000 hr.$^{-1}$.

The catalyst may be maintained in the contact area as fixed, moving or fluidized beds of solids. A fixed bed of solids is currently preferred for the method of this invention.

The catalyst may be maintained in the contact zone as fixed, moving a fluidized beds of solids. A fixed bed of solids is currently preferred for the method of this invention.

The effluent from the contact zone contains higher hydrocarbon products (e.g., ethylene, ethane and other light hydrocarbons), carbon oxides, water, unreacted hydrocarbon (e.g., methane) and oxygen, and other gases present in gas fed to the contact zone. Higher hydrocarbons may be recovered from the effluent and, if desired, subjected to further processing using techniques known to those skilled in the art. Unreacted methane may be recovered and recycled to the contact zone.

The invention is further illustrated by reference to the following examples. Experimental results reported below include conversions and selectivities calculated on a carbon mole basis. Ethylene/ethane ratios are shown as molar ratios.

EXAMPLE 1

A gaseous feedstream consisting of 50 vol. % air in methane and containing varying amounts of HCl was contacted with MgO (supplied by Kaiser Chemicals) and the results shown in Table I were obtained.

TABLE 1

CH$_4$/Air/HCl over MgO

| Vol % HCl in feed | Temp (°C.) | CH$_4$ GHSV (hr.$^{-1}$) | % CH$_4$ Conv. | % C$_2$+ Selectivity | C$_2$=/C$_2$ |
|---|---|---|---|---|---|
| 0 | 775 | 2400 | 16.0 | 33.1 | 0.56 |
| 0.05 | 775 | 2400 | 20.0 | 42.3 | 1.17 |
| 0.5 | 775 | 2400 | 29.6 | 68.9 | 6.14 |
| 1.0 | 775 | 2400 | 23.5 | 65.1 | 7.39 |
| 0 | 825 | 2400 | 16.9 | 42.2 | 0.96 |
| 0.05 | 825 | 2400 | 20.3 | 52.9 | 1.66 |
| 0.5 | 825 | 2400 | 29.3 | 71.9 | 5.50 |
| 1.0 | 825 | 2400 | 28.1 | 71.4 | 11.46 |
| 0 | 900 | 2400 | 20.6 | 48.9 | 2.57 |
| 0.5 | 900 | 2400 | 29.9 | 67.5 | 10.37 |
| 1.0 | 900 | 2400 | 26.9 | 72.0 | 20.75 |
| 0 | 800 | 4800 | 14.7 | 31.9 | 0.56 |
| 0.5 | 800 | 4800 | 29.1 | 69.8 | 5.00 |
| 1.0 | 800 | 4800 | 29.2 | 65.1 | 8.66 |
| 0 | 900 | 4800 | 19.9 | 55.2 | 1.39 |
| 0.5 | 900 | 4800 | 29.9 | 71.5 | 5.77 |

EXAMPLE 2

A gaseous feedstream consisting of 50 vol. % air in methane and containing 0.5 vol. % CHF$_3$ was contacted with MgO (supplied by Kaiser Chemicals) and the results shown in Table 2 were obtained.

TABLE 2

CH$_4$/Air/CHF$_3$ Over MgO

| Temp (°C.) | CH$_4$ GHSV (hr.$^{-1}$) | % CH$_4$ Conv. | % C$_2$+ Selectivity | C$_2$=/C$_2$ Ratio |
|---|---|---|---|---|
| 700 | 2400 | 2.9 | 35.5 | 0.1 |
| 750 | 2400 | 3.8 | 39.6 | 0.2 |
| 775 | 2400 | 5.9 | 50.9 | 0.4 |
| 825 | 2400 | 9.0 | 60.5 | 0.7 |
| 700 | 4800 | 2.5 | 85.0 | 3.1 |
| 750 | 4800 | 1.9 | 48.7 | 0.1 |
| 800 | 4800 | 3.3 | 64.7 | 0.6 |
| 900 | 4800 | 8.9 | 65.8 | 0.9 |

EXAMPLE 3

A gaseous feedstream consisting of 50 vol. % air in methane and containing 0.5 vol. % HCl was contacted with MgO (supplied by Catalyst Resources, Inc.) and the results shown in Table 3 were obtained.

TABLE 3

CH$_4$/Air/HCl Over MgO

| Temp (°C.) | CH$_4$ GHSV (hr.$^{-1}$) | % CH$_4$ Conv. | % C$_2$+ Selectivity | C$_2$=/C$_2$ Ratio |
|---|---|---|---|---|
| 775 | 2400 | 11.5 | 77.3 | 2.80 |
| 825 | 2400 | 20.7 | 64.8 | 7.05 |
| 900 | 2400 | 27.1 | 71.8 | 15.05 |
| 700 | 4800 | 0.8 | 88.6 | 0.16 |
| 750 | 4800 | 1.5 | 90.7 | 0.50 |
| 800 | 4800 | 6.3 | 90.8 | 1.59 |
| 900 | 4800 | 26.0 | 69.5 | 7.67 |

EXAMPLE 4

A gaseous feedstream consisting of 50 vol. % air in methane and containing 0.5 vol. % HCl was contained with CaO and the results shown in Table 4 were obtained.

TABLE 4

CH$_4$/Air/HCl Over CaO

| Temp (°C.) | CH$_4$ GHSV (hr.$^{-1}$) | % CH$_4$ Conv. | % C$_2$+ Selectivity | C$_2$=/C$_2$ Ratio |
|---|---|---|---|---|
| 700 | 2400 | 6.6 | 26.4 | 0.4 |
| 750 | 2400 | 15.1 | 35.9 | 0.7 |
| 775 | 2400 | 13.6 | 43.5 | 0.7 |
| 800 | 2400 | 18.7 | 46.7 | 1.1 |
| 900 | 2400 | 18.8 | 56.5 | — |
| 800 | 4800 | 15.6 | 62.2 | 2.7 |
| 900 | 4800 | 24.2 | 71.4 | 6.5 |

EXAMPLE 5

A gaseous feedstream consisting of 50 vol. % air in methane and containing varying amounts of HCl was contacted with La$_2$O$_3$ and the results shown in Table 5 were obtained.

TABLE 5

CH4/Air/HCl Over La2O3

| Vol % HCl in feed | Temp (°C.) | CH4 GHSV (hr.$^{-1}$) | % Conv. CH4 | % Conv. O2 | % Selectivity to: C2= | C2 | C2+ | CO | CO2 |
|---|---|---|---|---|---|---|---|---|---|
| 0.58 | 700 | 2400 | 18.5 | 88.4 | 6.8 | 16.3 | 24.2 | 39.9 | 35.9 |
| 0.58 | 750 | 2400 | 22.0 | 92.7 | 14.5 | 19.5 | 35.8 | 33.2 | 31.0 |
| 0.58 | 775 | 2400 | 22.1 | 93.4 | 18.8 | 20.3 | 41.3 | 29.2 | 29.5 |
| 0.58 | 800 | 2400 | 24.2 | 87.5 | 26.4 | 22.1 | 51.7 | 19.8 | 28.5 |
| 0.58 | 900 | 2400 | 24.6 | 93.0 | 36.8 | 16.1 | 57.0 | 19.1 | 23.9 |
| 0.5 | 700 | 4800 | 5.7 | 14.8 | 9.8 | 16.0 | 26.1 | 47.5 | 26.5 |
| 0.5 | 750 | 4800 | 8.8 | 22.5 | 22.4 | 17.1 | 40.9 | 38.8 | 20.3 |
| 0.5 | 800 | 4800 | 14.1 | 38.9 | 34.8 | 12.9 | 50.1 | 34.8 | 15.1 |
| 0.5 | 900 | 4800 | 23.8 | 78.1 | 41.2 | 7.1 | 51.7 | 36.4 | 11.9 |

EXAMPLE 6

A gaseous feedstream consisting of 50 vol. % air in methane and containing 0.5 vol. % HCl was contacted with TiO2 (anatase) and the results shown in Table 6 were obtained.

TABLE 6

CH4/Air/HCl Over TiO2

| Temp (°C.) | CH4 GHSV (hr.$^{-1}$) | % CH4 Conv. | % C2+ Selectivity | C2=/C2 Ratio |
|---|---|---|---|---|
| 750 | 2400 | 9.4 | 48.2 | 1.6 |
| 775 | 2400 | 14.2 | 45.3 | 2.6 |
| 825 | 2400 | 19.6 | 40.8 | 3.9 |
| 900 | 2400 | 20.2 | 32.0 | 3.2 |
| 700 | 4800 | 2.0 | 89.0 | 0.6 |
| 750 | 4800 | 4.0 | 92.7 | 1.3 |
| 800 | 4800 | 13.0 | 49.7 | 2.5 |
| 900 | 4800 | 18.8 | 36.5 | 2.9 |

EXAMPLE 7

A gaseous feedstream consisting of 50 vol. % air in methane and containing 0.5 vol. % HCL was contacted with SiO2 and the results shown in Table 7 were obtained.

TABLE 7

CH4/Air Over SiO2

| Temp (°C.) | CH4 GHSV (hr.$^{-1}$) | % CH4 Conv. | % C2+ Selectivity | C2=/C2 Ratio |
|---|---|---|---|---|
| 775 | 2400 | 1.7 | 94.7 | 1.52 |
| 825 | 2400 | 4.5 | 58.0 | 3.01 |
| 800 | 4800 | 0.66 | 100 | 0.93 |
| 900 | 4800 | 7.4 | 56.4 | 3.74 |

EXAMPLE 8

A gaseous feedstream consisting of 50 vol. % air in methane and containing 0.5 vol. % HCL was contacted with alpha-Al2O3 and the results shown in Table 8 were obtained.

TABLE 8

CH4/Air/HCl Over a-Al2O3

| Temp (°C.) | CH4 GHSV (hr.$^{-1}$) | % CH4 Conv. | % C2+ Selectivity | C2=/C2 Ratio |
|---|---|---|---|---|
| 700 | 2400 | 0.81 | 61.2 | 0.4 |
| 750 | 2400 | 2.8 | 39.7 | 0.7 |
| 775 | 2400 | 1.1 | 83.7 | 0.7 |
| 825 | 2400 | 1.7 | 88.6 | 1.4 |
| 900 | 2400 | 9.8 | 53.0 | 4.7 |
| 700 | 4800 | 0.28 | 63.1 | 0.3 |
| 750 | 4800 | 0.25 | 70.4 | 0.3 |
| 800 | 4800 | 0.43 | 83.1 | 0.5 |
| 900 | 4800 | 2.1 | 93.5 | 1.5 |

What is claimed is:

1. A method for converting methane to higher hydrocarbon products and coproduct water which comprises contacting a gas comprising methane and a gaseous oxidant with SiO2 at a temperature within the range of about 700° to 1200° C. in the presence of at least one gaseous promoter selected from the group consisting of halogens and compounds thereof, said contacting being conducted in the substantial absence of alkali metals and compounds thereof and in the substantial absence of reducible metal oxides.

2. The method of claim 1 wherein the promoter is selected from the group consisting of chlorine and mixtures thereof.

3. The method of claim 2 wherein the promoter is HCl.

4. The method of claim 2 wherein the promoter is an aliphatic chloride.

5. The method of claim 2 wherein the promoter is Cl2.

6. The method of claim 1 wherein the promoter is selected from the group consisting of bromine and compounds thereof.

7. The method of claim 6 wherein the promoter is HBr.

8. The method of claim 6 wherein the promoter is an aliphatic bromide.

9. The method of claim 6 wherein the promoter is is Br2.

10. The method of claim 1 wherein the gaseous oxidant comprises molecular oxygen.

11. The method of claim 1 wherein the gaseous oxidant comprises oxides of nitrogen.

12. The method of claim 11 wherein the oxides of nitrogen comprise N2O.

13. The method of claim 1 wherein the temperature is within the range of about 800° to 1000° C.

* * * * *